(12) United States Patent
Schürenberg et al.

(10) Patent No.: US 9,891,146 B2
(45) Date of Patent: Feb. 13, 2018

(54) PREPARATION OF THIN TISSUE SECTIONS FOR IMAGING MASS SPECTROMETRY

(71) Applicant: Bruker Daltonik GmbH, Bremen (DE)

(72) Inventors: Martin Schürenberg, Tarmstedt (DE); Jochen Franzen, Bremen (DE); Kai Rückriem, Bremen (DE); Eckhard Belau, Lilienthal (DE)

( * ) Notice: Subject to any disclaimer, the term of this patent is extended or adjusted under 35 U.S.C. 154(b) by 89 days.

(21) Appl. No.: 14/499,388

(22) Filed: Sep. 29, 2014

(65) Prior Publication Data
US 2015/0093780 A1 Apr. 2, 2015

(30) Foreign Application Priority Data
Oct. 2, 2013 (DE) .......................... 10 2013 016 299

(51) Int. Cl.
| | | |
|---|---|---|
| *G01N 1/30* | (2006.01) | |
| *G01N 1/40* | (2006.01) | |
| *H01J 49/04* | (2006.01) | |
| *G01N 1/31* | (2006.01) | |

(52) U.S. Cl.
CPC .............. *G01N 1/30* (2013.01); *G01N 1/4055* (2013.01); *H01J 49/0418* (2013.01); *G01N 1/31* (2013.01)

(58) Field of Classification Search
None
See application file for complete search history.

(56) References Cited

U.S. PATENT DOCUMENTS 5,584,486 A * 12/1996 Franklin ............. A63F 3/00157
273/274
2009/0166529 A1 7/2009 Shinma et al.

FOREIGN PATENT DOCUMENTS

| | | | |
|---|---|---|---|
| EP | 2317323 | A1 | 5/2011 |
| GB | 2437623 | A1 | 10/2007 |

OTHER PUBLICATIONS

Monroe, Eric B., et al. "Massively parallel sample preparation for the MALDI MS analyses of tissues." Analytical chemistry 78.19 (2006): 6826-6832.*
Bouschen, Werner, et al. "Matrix vapor deposition/recrystallization and dedicated spray preparation for high-resolution scanning microprobe matrix-assisted laser desorption/ionization imaging mass spectrometry (SMALDI-MS) of tissue and single cells." Rapid Communications in Mass Spectrometry 24.3 (2010): 355-364.*

* cited by examiner

*Primary Examiner* — Robert Yamasaki
(74) *Attorney, Agent, or Firm* — Benoît & Côté Inc.

(57) ABSTRACT

The invention relates to the preparation of thin tissue sections for mass spectrometric (MALDI) imaging, and proposes a method wherein a microcrystalline layer of the matrix material is produced on the surface of the thin tissue sections, and soluble analyte molecules are transported orthogonally through the thin tissue section to the matrix layer, without substantial lateral diffusion, by means of a solvent flow with alternating or constant direction, and are then deposited in the matrix layer and, if possible, embedded in the matrix crystals. A solvent flow which alternates in direction can be produced by successive, alternating phases of swelling and drying, brought about by periodic changes to the thin tissue section temperature and/or the partial pressures of the solvents. A continuous solvent flow can be generated by applying the thin tissue section onto a porous support which supplies solvent to the rear surface of the thin tissue section.

17 Claims, 1 Drawing Sheet

PREPARATION OF THIN TISSUE SECTIONS FOR IMAGING MASS SPECTROMETRY

BACKGROUND OF THE INVENTION

Field of the Invention

The invention relates to the preparation of thin tissue sections for mass spectrometric imaging with ionization by matrix-assisted laser desorption (MALDI), particularly for high-resolution and high-sensitivity imaging of soluble peptides and proteins.

Description of the Related Art

Imaging mass spectrometry (imaging MS or IMS) acquires images of thin tissue sections which shows for every pixel the mass spectrum of the ionizable components, corresponding to the color spectrum in every pixel of an optical image. The ionization is usually carried out by matrix-assisted laser desorption (MALDI), not least because MALDI primarily produces singly charged molecular ions, which means that the resulting mass spectra are very easy to interpret.

Several methods are known for the preparation of thin tissue sections in imaging mass spectrometry with MALDI, particularly spray methods for matrix solutions. For example, the patent family U.S. Pat. No. 7,667,196 B2, GB 2437623 B and DE 10 2006 019 530 B4 (M. Schürenberg et al.) discloses a method of applying the matrix by depositing isolated droplets of a thin mist of matrix solution, with intermediate drying phases. The individual droplets each bring solvent, which penetrates into the thin tissue section and, via the subsequent vaporization, transports analyte molecules from the thin tissue section to the matrix layer. Unfortunately, the liquid of each droplet spreads radially in all directions, so the analyte substances are also transported laterally within the thin tissue section; this limits the spatial resolving power of the image because the spatial information of the analyte molecules is smeared out.

It is furthermore known that the matrix material can also be applied by resublimation, see for example "Sublimation as a Method of Matrix Application for Mass Spectrometric Imaging", J. A. Hankin et al., J. Am. Soc. Mass Spectrom. 2007, 18/9, 1646-1652. This method is particularly suitable for phospholipids because their outstandingly good ionizability means that they always display a high sensitivity. The sensitivity for peptides is low, however, because hardly any peptide molecules are embedded into the matrix layer. Only analyte molecules from the topmost molecular layer of the thin tissue section can be captured because the dry application of the matrix layer does not involve a transport of analyte substances from the thin layer to the matrix layer. The consequence of this is that only a small number of analyte molecules are formed during laser bombardment in the course of an ionization with matrix-assisted laser desorption, and the signal-to-noise ratio is unfavorably low at the ion detector.

It is also known that, in a moisture chamber, the swelling of a thin tissue section with a matrix layer applied in the dry state causes small quantities of peptides and proteins to be transferred by diffusion from the volume of the thin tissue section close to the surface into the matrix layer. However, this slow diffusion of the analyte molecules to the matrix layer in the swollen thin tissue section is also associated with an undesirable lateral diffusion of the analyte molecules in the same order of magnitude, which in turn smears out the spatial information of the analyte molecules.

In view of the foregoing, there is a need for a method whereby larger quantities of soluble analyte molecules are transported from the depth of the thin tissue section (i.e. not only from the layers in the immediate vicinity of the surface) into the matrix layer, which may already exist or may be growing at the same time, substantially without lateral diffusion of the analyte molecules.

SUMMARY OF THE INVENTION

The invention proposes a method wherein a microcrystalline layer of the matrix material is applied to the surface of the thin tissue sections, and the soluble analyte molecules, preferably soluble peptides and proteins, but also other substances such as pharmaceutical products, are transported straight through the thin tissue section, without substantial lateral diffusion, to the matrix layer by means of a solvent flow with alternating or constant direction, which preferably does not dissolve the matrix layer, and are then deposited there into the matrix layer and, if possible, embedded into the matrix crystals. It is known that many types of matrix crystal can bind peptides and proteins relatively firmly on the surface. It is most advantageous to carry out the transport while the matrix crystals are growing, or in breaks between growth phases, so that the analyte molecules can immediately be immovably embedded in the matrix crystals. A solvent flow which alternates in direction can be produced by successive, alternating phases of swelling and drying, brought about by periodic changes to the thin tissue section temperature and/or the partial pressures of the solvents. A continuous solvent flow can be generated by applying the thin tissue section onto a porous support which supplies solvent to the rear surface of the thin tissue section. The matrix layer can grow by phased resublimation, for example, preferably on crystal nuclei applied in advance, and also by applying an almost dry matrix snow, generated by electrospraying, for example.

The matrix layer can be produced by resublimation at atmospheric pressure (approx. $10^5$ to $10^4$ pascal) or at a reduced pressure (less than $10^4$ pascal), for example. In the latter case, the resublimation must, of course, be carried out in a gas-tight and suitably evacuated chamber. The sublimation of the matrix material can be done continuously or periodically (i.e. regularly repeated). The use of crystallization nuclei, which are applied to the thin tissue section before the matrix material, can produce a dense, only slightly porous layer of tiny microcrystals. The dry matrix layer can also be applied in a different way, however, such as by generating and depositing a snow of small matrix crystals, for example by electrospraying a matrix solution with immediate drying of the droplets after they have exited from the spray capillary before the snow is deposited on the surface of the thin tissue section.

A flow of solvent whose direction alternates can be achieved by successively alternating the conditions for swelling in a vapor of at least one solvent and for drying of the thin tissue section. The solvents which can be advantageously used are those which cannot dissolve the matrix crystals; but this is not an absolute requirement. "Swelling in the vapor of a solvent" here means that no layer with a liquid phase in which the analyte molecules could redissolve is produced at the surface, but rather a condensation into the thin tissue section takes place and causes it to swell. The conditions for the swelling and drying can be set by means of the temperature of the thin tissue section and/or by the partial pressures of the solvent in the gas above the thin tissue section. If they are altered periodically, phases of swelling of the thin tissue section can alternate with phases of drying, with the direction of liquid flow alternating inside the thin tissue section. The temperature of the thin tissue section can, for example, be changed by a Peltier element which is located at the side of the sample support facing away from the thin tissue section and supplies heat to, or removes it from, the thin tissue section via the heat-conducting (e.g. metal) sample support. During the drying phases, dissolved peptides and proteins are transported to the matrix layer. If these are firmly embedded into the matrix layer or firmly bound to the surface of the matrix crystals, only pure solvent without any dissolved analyte molecules will penetrate into the thin tissue section during the swelling phase. Water, acetonitrile or a mixture of both can be used as the solvent, for example. If two or more solvents are used, the partial pressures can be set in such a way that the swelling conditions for the components of the mixture correspond to a desired ratio.

For the drying phases, it is favorable if a liquid film forms between the crystals of the matrix layer, by the temperature falling below the dew point, for example, and this liquid film allows the soluble analyte substances to migrate to the surface of the crystals and be adsorbed there. The liquid film can originate from the same liquid as the solvent which causes the swelling, but it can also be a different solvent.

A continuous flow of solvent straight through the thin tissue section can be achieved by applying the thin tissue section onto a porous support, which can be soaked with solvent in such a way that the drying of the solvent has to occur through the thin tissue section. There are many different microporous and nanoporous materials, made of glass, ceramic, plastic or metal. It is expedient here to seal the porous surface around the thin tissue section, and also the rear of the porous material if necessary, so that it becomes practically impenetrable to the solvent. A drop of solvent can be absorbed by the porous support and be distributed in the porous material by capillary forces.

In order to measure peptides and proteins efficiently, it is helpful to rinse the lipids out of the thin tissue section before the preparation using methods that are basically known.

DETAILED DESCRIPTION

Figure 1:
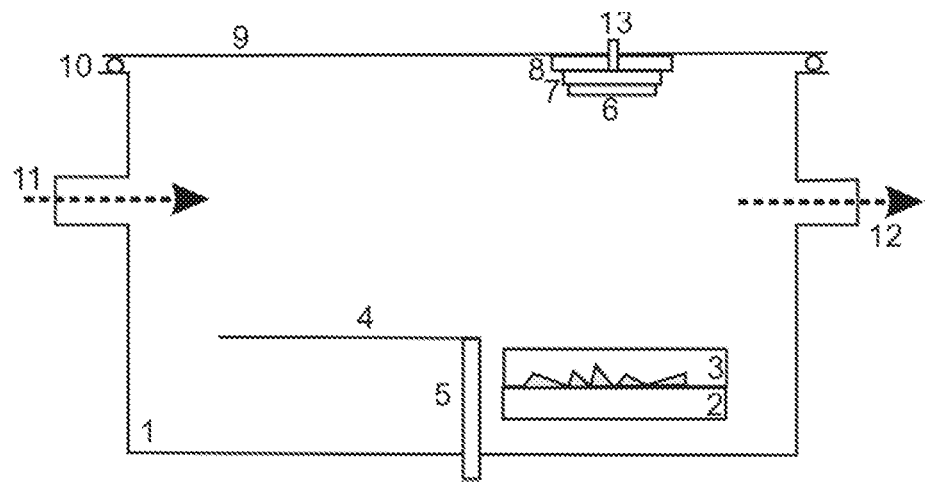
FIG. 1 shows a schematic example of a sublimation chamber (1), with a sublimation dish (3) which is filled with matrix material and can be heated by a heater (2). The sublimation dish (3) can be temporarily closed by a lid (4), which can be rotated and lowered by the shaft (5). The resublimation takes place on a thin tissue section (6), which is located on a support (7). The support (7) can be heated and cooled by the Peltier element (8). The seals (10) can seal the lid (9) so that an evacuation of the sublimation chamber is possible. The sublimation chamber can be evacuated via the outlet (12); solvent vapors can be fed in via the inlet (11). The complete sublimation chamber (1) can be heated to prevent resublimation on the chamber's inner surfaces and to direct it only onto the support (7) of the thin tissue section. If the support (7) consists of porous material, a solvent can be fed to it through the inlet (13).

As has already been described, the invention proposes that special methods be used to produce a dense, but porous microcrystalline layer of the matrix material on the surface of the thin tissue sections, and to transport the soluble peptides and proteins and other analyte substances (preferably not including lipids) straight from the thin tissue section to the matrix layer by means of a solvent flow, whose direction alternates or remains constant, and to bind them into the matrix layer. The flow of solvent should take place uniformly, straight through the thin tissue section so that no significant lateral diffusion takes place which could smear out the spatial information of the analyte molecules. Thin tissue sections are around 10 to 20 micrometers thick. The objective is to achieve a pixel resolution of better than around 20 micrometers, preferably down to five micrometers. For such a high pixel resolution, ionization by matrix-assisted laser desorption (MALDI) requires the spot diameters of the laser beam to be small, which in turn requires as high a concentration of analyte molecules as possible in the matrix layer in order to produce an analytically useful image.

The matrix layer should, if possible, be applied dry in order to avoid lateral flows of solvents and any lateral transport of analyte molecules within the thin tissue section and on its surface. Another reason why a dry method of producing the matrix layer is favorable is that it allows the partial pressures of solvents in the gas, which are used for the swelling or the transport of analyte molecules, to also be adjusted in the space above the thin tissue section without interference. An independent adjustment of the partial pressures of the solvents would be almost impossible when working with a deposition of wet spray-mist droplets.

In order to measure peptides and proteins efficiently, it is useful to first carefully rinse out the lipids from the thin tissue section, using methods that are essentially known, because otherwise the mass signals of the lipids could overlie all other mass signals with such a high intensity that it becomes difficult to evaluate the mass spectra. Rinsing out the lipids corresponds to the prior art. It can preferably be carried out with solvents which do not dissolve any analyte molecules.

In one embodiment of the matrix layer formation, the matrix layer can, for example, be produced by resublimation of sublimed matrix material at atmospheric pressure (approx. $10^5$ to $10^4$ pascal), at a reduced pressure ($10^4$ to $10^2$ pascal), or in a technical vacuum (less than $10^2$ pascal). In a sublimation unit, the matrix material can be introduced into the resublimation chamber as a vapor by continuous or periodic sublimation of the matrix material. The aim is to produce a layer of microcrystals in the order of around one micrometer thick or less which densely covers the surface of the thin tissue section, but is nevertheless porous. Matrix layers produced according to the prior art, either with spraying methods or by resublimation, usually form islands several micrometers in diameter, with gaps in between; such a layer is unfavorable for high-resolution imaging. Special measures therefore have to be taken in order to produce a dense, but porous covering. The porosity is conducive to the embedding of analyte molecules.

The use of crystallization nuclei on the thin tissue section can support a dense crystallization during the resublimation. It is known, for example, that the matrix substance CHCA (α-cyano-4-hydroxycinnamic acid) crystallizes out in a very fine and dense manner on extremely fine particles of graphite, at least on a metal substrate (see J. Gorka et al.: "Graphite supported preparation of alpha-Cyano-4-Hydroxycinnamic Acid (CHCA) for matrix-assisted laser desorption/Ionization mass spectrometry", J Am Soc Mass Spectr 23: 1949-1954). But it is also possible to use other crystallization nuclei, for example very finely ground minerals which have the same lattice constants and crystal shapes as the matrix substance. It is even possible to apply the very finely ground matrix substance itself in nano-powder form to the dried thin tissue section using a shaving brush, and then press it down firmly in order to initiate a dense growth of extremely fine matrix crystals. The powdery excess of the second and third layer can be removed by blowing on it with some force. In order to control the degree of porosity, other nano-powders can be admixed with the matrix powder, for example fine-crystalline cellulose, which allows a desired separation between the matrix crystal nuclei to be set.

On the other hand, it also appears possible to produce complexes of matrix molecules with solvent molecules by means of solvent vapors in the resublimation chamber. These complexes then produce particularly fine and porous matrix layers during the crystallization.

There are also other methods for the dry application of matrix layers, however. In a further embodiment of matrix layer formation, it is possible to spray matrix solutions and allow the droplets to dry after they leave the spray nozzle so that a fine crystal snow is produced, which can be deposited on the thin tissue section. An electrospray method, in particular, can be used for this. The deposited snow is initially very powdery, but by adding a solvent in vapor form and lowering the temperature to below the dew point it is possible to produce a 'wet' snow (or firn) from the powder snow, and this forms a solid, porous matrix layer when it dries.

The matrix layer has, to date, often been produced at atmospheric pressure; but it is also possible to use lower pressure or even a technical vacuum.

A thin tissue section is a complex collection of substances, particularly soluble and insoluble polymers, predominantly peptides and proteins, some cross-linked, some not cross-linked. The cross-linked components, for example the residues of the cell membranes or vessel walls, form a strongly inhomogeneous structure. The thin tissue section can swell in different solvents, for example in water, but also in alcohols. The liquid in the swollen thin tissue section can be considered to be a separate physical state, which is between the phases of "solid" and "liquid". Many of the solvent molecules are bonded to polar groups of the polymer molecules by hydrogen bridges. The consequence is that the vapor pressure over a swollen thin tissue section is reduced compared to the vapor pressure over a liquid with the same temperature, and also depends on the concentration of the solvent in the swollen thin tissue section.

To generate the solvent flow straight through the thin tissue section, in one embodiment a solvent flow with alternating direction is generated by periodically changing the conditions for the swelling and drying of the thin tissue section. The swelling creates a solvent flow into the thin tissue section; the drying creates a flow out of the thin tissue section. We call this "solvent flow", although it is a mixture of a flow of the solvent through the structures of the cross-linked components of the thin tissue section and a directed diffusion caused by a steep concentration gradient, but where the transport of material into the thin tissue section (or out of the thin tissue section) exceeds the purely thermal diffusion in the lateral direction by orders of magnitude. This periodic swelling and drying can be combined with the continuous or periodic growth of the matrix crystal layer in a variety of ways in order to bind the analyte molecules in the matrix layer.

In order for swelling phases and drying phases to alternate, the temperature of the thin tissue section can be periodically lowered and/or the partial pressures of the solvents involved can be periodically increased. The temperature of the thin tissue section can be changed by a Peltier element, for example, which is located on the rear of the sample support. The partial pressures of the solvents used can be changed by feeding in solvent vapor, but also by increasing the total pressure, for example. If, for instance, the gas volume in which the thin tissue section is located is compressed from ten liters to half a liter, all the partial pressures also increase by a factor of 20.

During the drying phases, soluble non-cross-linked peptides and proteins are transported with the solvent flow out of the thin tissue section to the matrix layer on the surface of the thin tissue section, because it is only here (apart from the narrow sides of the thin tissue section, which have a very small surface area) that a transition of the solvent into the gaseous phase is possible. These peptides and proteins can be adsorptively bound to the surface of the matrix crystals or even firmly embedded into the growing matrix layer. This means that, during the phases of swelling, only pure solvents without any dissolved analyte substances penetrate into the thin tissue section.

For the drying phases, it can be favorable for a film of liquid to form in the pores between the crystals of the matrix layer, thus making it possible for the soluble analyte substances to migrate from the surface of the thin tissue section to the surface of the crystals, where they can be adsorbed. Hence, whereas a liquid film is to be avoided during the swelling, it can be desirable during the drying. The liquid film can be formed from the solvent which is responsible for the swelling, or it can be a special transport solvent. The liquid film can, for example, be produced by reducing the temperature to below the dew point for this transport solvent so that the swelling solvent then vaporizes through this transport solvent. If the swelling solvent is an alcohol, for example, then the transport solvent can be a very volatile oil which does not contribute to the swelling, but in which the alcohol can dissolve.

Water, methanol, ethanol, acetonitrile, or mixtures of these, for example, can be used as the solvent to swell the thin tissue section. If several solvents are used, the partial pressures in the atmosphere over the thin tissue section can be adjusted in such a way that all components of the mixture are involved in the swelling of the thin tissue section, and in desired percentages. If a sublimation unit is used, it is preferably equipped with a device for regulating the partial pressures of the solvents used. Lowering the vapor pressure above the swelling material causes the swelling to already start far above the dew point which applies to a solvent on a non-swelling surface. This can be used, if desired, to avoid the formation of dew, i.e. condensation of the vapor to a liquid on the surface; on the other hand, it is also possible to force the formation of dew.

If water is used as the solvent, for example, and if the gas which transfers the sublimation vapors is maintained at an easily controllable temperature of 30° Celsius, the dew-point temperature is 18° Celsius for a relative humidity of 50%. A similar dew-point temperature is achieved with 40% acetonitrile. If, therefore, the temperature of the sample support carrying the thin tissue section is lowered to a value below 18° Celsius, dew will form with both water and acetonitrile at the same time.

In a different embodiment for generating a solvent flow, a continuous solvent flow straight through the thin tissue section is achieved by applying the thin tissue section onto a porous support which can be soaked with solvents. By suitably covering the exposed areas of the porous support outside the thin tissue section, it is possible to ensure that the vaporization of the solvent can largely take place only on the surface of the thin tissue section, thus forcing a solvent flow through the thin tissue section. For example, it is possible to seal the porous surface around the thin tissue section, and also the rear of the porous material if necessary, with a lacquer which does not penetrate into the pores. It is often sufficient to apply a film, preferably a moist film (of plastic, for example) which adheres firmly after drying. The back of the porous support can also be sealed by laying on a glass sheet.

There are many types of open-pore material (i.e. not closed-cell foams), made of glass, ceramic, plastic, or metal, with pore diameters down to a few nanometers. A drop of solvent is eagerly sucked up by many porous materials and distributed in the porous material by capillary action. But there are also porous materials whose surface properties do not allow the solvent to be absorbed. A plate of this material can also be used to seal the back, which has the particular advantage that air can flow through the porous sealing plate before passing through the thin tissue section as the porous support is drying. Consequently, there are no longer any lateral flows in the porous support either, after an initial distribution phase. The flow of the solvent through the thin tissue section can be controlled to a certain extent by controlling the temperature.

It is to be noted here that the terms "nanoporous" and "microporous" are used in the literature in a confusing way. In the older literature, the term "microporous" is defined as meaning pore sizes of less than two nanometers, "mesoporous" is used for pore sizes between 2 and 50 nanometers, and "macroporous" for pore sizes above 50 nanometers. In more recent literature, however, "nanoporous" can be found for pore diameters of one to several hundred nanometers, usually for new synthetic materials from "nanotechnology research" programs.

The different embodiments for the generation of the solvent flows and for the production of the matrix layer comprise fundamentally different embodiments of the apparatus used in each case.

In a first embodiment of the apparatus, as depicted in FIG. 1, the matrix substance is sublimed in a heated pan (3) on the floor of a chamber (1), while the thin tissue section (6) is located on a support (7) hanging from the lid at the top. The walls of the chamber (1) can be heated in such a way that no resublimation takes place there. The thin tissue section (6) on its support (7) can be cooled or heated to a specific temperature, by a Peltier element (8), for example. The matrix crystal layer is fed with matrix vapor from below. The chamber (1) can be charged with the vapors of the solvents for the swelling via an inlet (11), and can also be evacuated, if required, via the outlet (12).

In this first embodiment apparatus, a special preparation method may be performed. This special method uses a solvent which at the same time can swell the thin tissue section, transport peptides, and solve a part of the matrix layer for a recrystallization with embedding the peptides into the crystals. After mounting the slide with the thin tissue section (6) to the Peltier element (8) and filling the pan (3) with a distinct amount of matrix material, the method comprises the steps: (a) evacuating the chamber down to a few hectopascals through the outlet (12) and closing the pumping line, (b) cooling the thin tissue section (6) below room temperature, (c) creating a matrix layer on the thin tissue section (6) by sublimation and resublimation of the matrix material in pan (3), (d) injecting a certain amount of solvent to generate a distinct partial pressure via inlet (11), thereby creating a distinct partial pressure of the solvent in the chamber, (e) cooling the thin tissue section (6) with the Peltier element (8) to the dew point for a distinct time period, whereby a part of the matrix layer is solved and the thin tissue section is swollen by soaking a distinct amount of the solvent vapor, then (f) increasing the temperature of the thin tissue section and pumping away the solvent vapor, whereby the matrix layer is recrystallized and analytical molecules from the depth of the thin tissue section are embedded in the crystals. In this special method, in a single period of swelling, enough analytical material is transported to achieve neat mass spectra; and the space resolution remains extraordinarily high.

If the thin tissue section (6) is on a porous support (7), then in this position the continuous-direction solvent flow through the thin tissue section can also be realized by soaking the porous support (7) with solvent through the inlet (13).

The sublimation and resublimation can also be (if wanted, periodically) interrupted by a heated lid (4) which can be swiveled over the pan (3), for example, in order to allow the solvent flows to act without simultaneous resublimation. A different means of moving the lid (4), for example a hinge, can also be used. The closing of the sublimation dish (3) can be particularly important if, during the drying, a film of moisture is to be produced in the matrix layer by lowering the temperature to below the dew point for one or more solvents, and in this moisture film the analyte molecules are able to migrate to the surface of the tiny matrix crystals.

Figure 2:
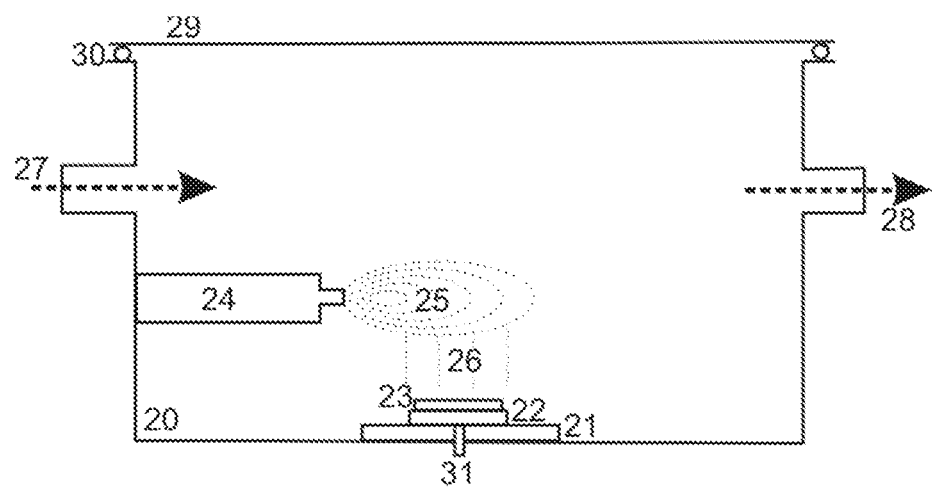
FIG. 2 is a schematic representation of a chamber (20) in which a sprayer (24) can generate a fine cloud of droplets (25), from which a dry snow (26) of matrix material falls onto the support plate (22) with the thin tissue section (23) after the droplets have dried. The Peltier element (21) can heat or cool the thin tissue section. If the support (22) consists of porous material, solvent can be fed in via the inlet (31). The gas mixture in the chamber and its pressure can be adjusted via inlet (27) and outlet (28).

In a second embodiment of the apparatus, which is schematically depicted in FIG. 2, the thin tissue section (23) on its support (22) is located near the floor of a chamber (20). In this position, the matrix snow (26) can be applied by a sprayer (24), for example. To ensure the snow is applied uniformly, it must be possible to move the support (22) for the thin tissue section (23) in a variety of ways. Here again, the thin tissue section (23) on its support (22) should be able to be heated and cooled, by the Peltier element, for example. It is also possible here to feed in vapors of solvents or other working gases, such as inert nitrogen $N_2$, via the inlet (27); the pressure can be regulated via the outlet (28). For example, a solvent can be fed in which forms a floor-level mist above the cold thin tissue section on the support (22). This mist slightly dissolves the matrix crystals of the snow and thus incorporates the analyte molecules into the matrix crystals during the subsequent recrystallization. A floor-level mist can also help to transport the analyte molecules from the surface of the tissue to the matrix crystals.

The invention has been shown and described with reference to a number of different embodiments thereof. It will be understood, however, that various aspects or details of the invention may be changed, or various aspects or details of different embodiments may be arbitrarily combined if practicable, without departing from the scope of the invention. Furthermore, the foregoing description is for the purpose of illustration only, and not for the purpose of limiting the invention, which is defined solely by the appended claims.

The invention claimed is:

1. A method for the preparation of a thin tissue section whose surface is provided with a matrix layer for the acquisition of a mass-spectrometric image using ionization by matrix-assisted laser desorption, the method comprising transporting analyte molecules from various layers of the thin tissue section straight through the thin tissue section to the matrix layer at the surface of the thin tissue section by means of generating a solvent flow with alternating direction, which solvent flow is generated by alternate swelling and drying of the thin tissue section brought about by one of changing the partial pressure of a solvent in the ambient gas, changing a temperature of the thin tissue section, and changing both the temperature and the partial pressure, wherein the method is carried out in a chamber in which an ambient gas pressure is kept that is below atmospheric pressure.

2. The method according to claim 1, wherein the ambient gas pressure in the chamber is kept at less than $10^4$ pascal.

3. The method according to claim 1, wherein the temperature of the thin tissue section or the partial pressure of the solvent in the ambient gas are changed such as to avoid the formation of dew on the thin tissue section.

4. The method according to claim 1, wherein the partial pressure is changed by compressing the gas volume.

5. The method according to claim 1, wherein the partial pressure is changed by alternately feeding-in solvent vapor and neutral gas.

6. The method according to claim 1, wherein several solvents are used to transport the analyte molecules, and the partial pressures of the individual solvents are controlled in such a way that each solvent participates in the swelling of the thin tissue section.

7. The method according to claim 1, wherein the matrix layer is applied to the tissue section in the chamber, and wherein the solvent flow is generated alternatingly with the application of the matrix layer.

8. The method according to claim 1, wherein the matrix layer is applied to the tissue section in the chamber, and wherein the solvent flow is generated while the matrix layer is growing.

9. The method according to claim 1, wherein the matrix layer is applied by resublimation in the chamber.

10. The method according to claim 9, wherein the resublimation is assisted by crystal nuclei, which are applied to the thin tissue section before the resublimation.

11. The method according to claim 10, wherein the crystal nuclei consist of a fine crystalline powder whose lattice constant and crystal shapes are similar to the crystals of the matrix substance.

12. The method according to claim 10, wherein the crystal nuclei consist of fine matrix crystal powder.

13. The method according to claim 1, wherein during the phases where the solvent flow in the thin tissue section transports the analyte molecules to the matrix layer, a liquid film is produced in the matrix layer, in which the analyte molecules can reach the surface of the matrix crystals.

14. The method according to claim 1, wherein the matrix layer is applied, after locating the tissue section in the chamber, as snow generated by spraying a matrix solution with immediate drying of droplets after they have exited from a spray capillary before the resultant snow is deposited on the surface of the thin tissue section.

15. The method according to claim 14, wherein the snow is stuck together by condensation of a solvent.

16. The method according to claim 1, wherein the matrix layer comprises a material applied dry to the thin tissue section in order to avoid lateral flows of solvents and any lateral transport of analyte molecules within the thin tissue section and on its surface.

17. The method according to claim 16, wherein the application of the dry matrix layer and the alternate swelling and drying of the thin tissue section are conducted in the chamber.

* * * * *